US00PP14139P29

(12) United States Plant Patent
Kretz et al.

(10) Patent No.: US PP14,139 P2
(45) Date of Patent: Sep. 16, 2003

(54) LYCHNIS PLANT NAMED 'LYCHJEN'

(75) Inventors: Rainer Kretz, Blandford Forum (GB); Paul Gooderham, Diss (GB)

(73) Assignee: Blooms of Bressingham Ltd., Bressingham (GB)

( * ) Notice: Subject to any disclaimer, the term of this patent is extended or adjusted under 35 U.S.C. 154(b) by 0 days.

(21) Appl. No.: 10/142,839

(22) Filed: May 10, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—June Hwu
(74) *Attorney, Agent, or Firm*—C. A. Whealy

(57) ABSTRACT

A distinct cultivar of Lychnis plant named 'Lychjen', characterized by its upright plant habit; freely basal clumping growth habit; freely flowering habit; and bright pink-colored double flowers.

1 Drawing Sheet

BOTANICAL CLASSIFICATION/CULTIVAR DESIGNATION

*Lychnis flos-cuculi* cultivar Lychjen.

BACKGROUND OF THE INVENTION

The present Invention relates to a new and distinct cultivar of Lychnis plant, botanically known as *Lychnis flos-cuculi,* and hereinafter referred to by the cultivar name 'Lychjen'.

The new Lychnis originated from a chance cross-pollination of two unidentified selections of *Lychnis flos-cuculi,* not patented. The cultivar Lychjen was discovered and selected by the Inventors as a flowering plant within the progeny of the stated cross in a controlled environment in 1994 in Blandford Forum, Dorset, United Kingdom.

Asexual reproduction of the new cultivar by divisions and basal cuttings taken at Bressingham, United Kingdom, since April, 1995, has shown that the unique features of this new Lychnis are stable and reproduced true to type in successive generations.

SUMMARY OF THE INVENTION

Plants of the cultivar Lychjen have not been observed under all possible environmental conditions. The phenotype may vary somewhat with variations in environment such as temperature and light intensity without, however, any variance in genotype.

The following traits have been repeatedly observed and are determined to be the unique characteristics of 'Lychjen'. These characteristics in combination distinguish 'Lychjen' as a new and distinct cultivar:

1. Upright plant habit.
2. Freely basal clumping growth habit, dense and bushy plants.
3. Freely flowering habit.
4. Bright pink-colored double flowers.

Plants of the new Lychnis differ from plants of the parent selections and other selections of *Lychnis flos-cuculi* in the following characteristics:

1. Plants of the new Lychnis are more compact than plants of the parents and other selections of *Lychnis flos-cuculi.*

2. Plants of the new Lychnis are more freely basal clumping than plants of the parents and other selections of *Lychnis flos-cuculi.*
3. Plants of the new Lychnis are more freely flowering than plants of the parents and other selections of the *Lychnis flos-cucli.*
4. Plants of the new Lychnis have larger flowers than plants of the parents and other selections of *Lychnis flos-cuculi.*
5. Plants of the new Lychnis have double flowers whereas plants of the parents and other selections of *Lychnis flos-cuculi* have single flowers.
6. Plants of the new Lychnis do not set seed whereas plants of the parents and other selections of *Lychnis flos-cuculi* readily set seed.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ from the color values cited in the detailed botanical description which accurately describe the colors of the new Lychnis.

The photograph at the top of the sheet comprises a side perspective view of typical plants of 'Lychjen' grown in the landscape for two growing seasons.

The photograph at the bottom of the sheet comprises a close-up view of typical inflorescences of 'Lychjen'.

DETAILED BOTANICAL DESCRIPTION

In the following description, color references are made to The Royal Horticultural Society Colour Chart, 1995 Edition, except where general terms of ordinary dictionary significance are used. Plants were grown in Bressingham, United Kingdom under outdoor field conditions which closely approximate commercial production conditions. During the production of the plants, day temperatures ranged from 5 to 28° C. and night temperatures ranged from −8 to 15° C. Plants used for the description were grown for two growing seasons in 5-liter containers.

Botanical classification: *Lychnis flos-cuculi* cultivar Lychjen.

Parentage:

*Female, or seed, parent.*—Unidentified selection of *Lychnis flos-cuculi,* not patented.

*Male, or pollen, parent.*—Unidentified selection of *Lychnis flos-cuculi,* not patented.

Propagation:

*Type.*—By basal cuttings.

*Time to initiate roots.*—About 10 days at 20° C.

*Time to produce a rooted cutting.*—About 25 days at 20° C.

*Root description.*—Fibrous, thin, grayed white in color.

*Rooting habit.*—Freely branching, dense.

Plant description:

*Plant form.*—Upright and freely basal clumping perennial; dense and bushy plants; leaves, basal; flowering stems arise from the root crown.

*Usage.*—Appropriate for use as a border plant and in containers.

*Plant height, soil level to top of flowers.*—About 75 cm.

*Plant width.*—About 45 cm.

*Foliage description.*—Arrangement: Simple, basal; sessile. Length: About 15 cm. Width: About 2.5 to 3 cm. Shape: Oblanceolate. Apex: Acute. Base: Cuneate. Margin: Entire. Texture, upper surface: Rough; slightly pubescent. Texture, lower surface: Rough; glabrous. Venation pattern: Reticulate. Color: Young foliage, upper surface: 145A flushed with 181A. Young foliage, lower surface: 145B. Fully expanded foliage, upper surface: 137A. Fully expanded foliage, lower surface: 138B. Venation, upper surface: 138C. Venation, lower surface: 139C.

Flower description:

*Flower type and habit.*—Double flowers with reproductive organs transformed into petal-like structures; flowers arrange in compound dichasial cymes on long basal flowering stems. Flowering stems, erect to slightly outwardly spreading; flowers face mostly upright. Flowers persistent.

*Fragrance.*—None detected.

*Natural flowering season.*—Continuously flowering from May to September in Bressingham, United Kingdom.

*Quantity.*—Freely flowering with about 20 flowers and flower buds per flowering stem or about 384 flowers per plant.

*Flower longevity.*—About four weeks.

*Flower diameter.*—About 3 to 4 cm.

*Flower depth (height).*—About 3 cm.

*Flower buds.*—Length: About 1 cm. Diameter: About 8 mm. Shape: Obtuse. Color: 73B.

*Petals.*—Arrangement/appearance: More than 35 petals arranged in a rosette. Length: About 2 cm. Width: About 1.5 cm. Shape: Flabellate. Apex: Emarginate. Margin: Entire. Texture, upper and lower surfaces: Smooth; satiny. Color: When opening, upper surface: 73B. When opening, lower surface: 73C. Fully opened, upper surface: Outer petals, 62A becoming closer to 62C with subsequent development; inner petals, 157C, becoming closer to 62C with subsequent development. Fully opened, lower surface: Outer petals, 62B; inner petals, 157D.

*Calyx.*—Arrangement: Tubular, five fused sepals. Length: About 1 cm. Diameter: About 5 mm.

*Flowering stems.*—Length: About 75 cm. Diameter at the base of the plant: About 2.5 cm. Strength: Strong. Angle: Mostly erect to slightly outwardly spreading. Texture: Smooth, glabrous. Color: 139C.

*Peduncles.*—Length: About 5 cm. Diameter: About 2 mm. Strength: Strong. Angle: About 45° from vertical. Texture: Smooth, glabrous. Color: 139C.

*Pedicels.*—Length: About 2 cm. Diameter: About 1.5 mm. Strength: Strong. Angle: About 45° from vertical. Texture: Smooth, glabrous. Color: 139C flushed with 181A.

*Reproductive organs.*—None observed.

*Seed/fruit.*—Seed and fruit production have not been observed.

Disease/pest resistance: Under commercial production conditions, plants of the new Lychnis have not been noted to be resistant to pathogens or pests common to Lychnis.

Weather/temperature tolerance: Plants of the new Lychnis have been observed to tolerate rain, wind, and temperatures from −8 to 28° C. in Bressingham, United Kingdom.

It is claimed:

1. A new and distinct cultivar of Lychnis plant named 'Lychjen', as illustrated and described.

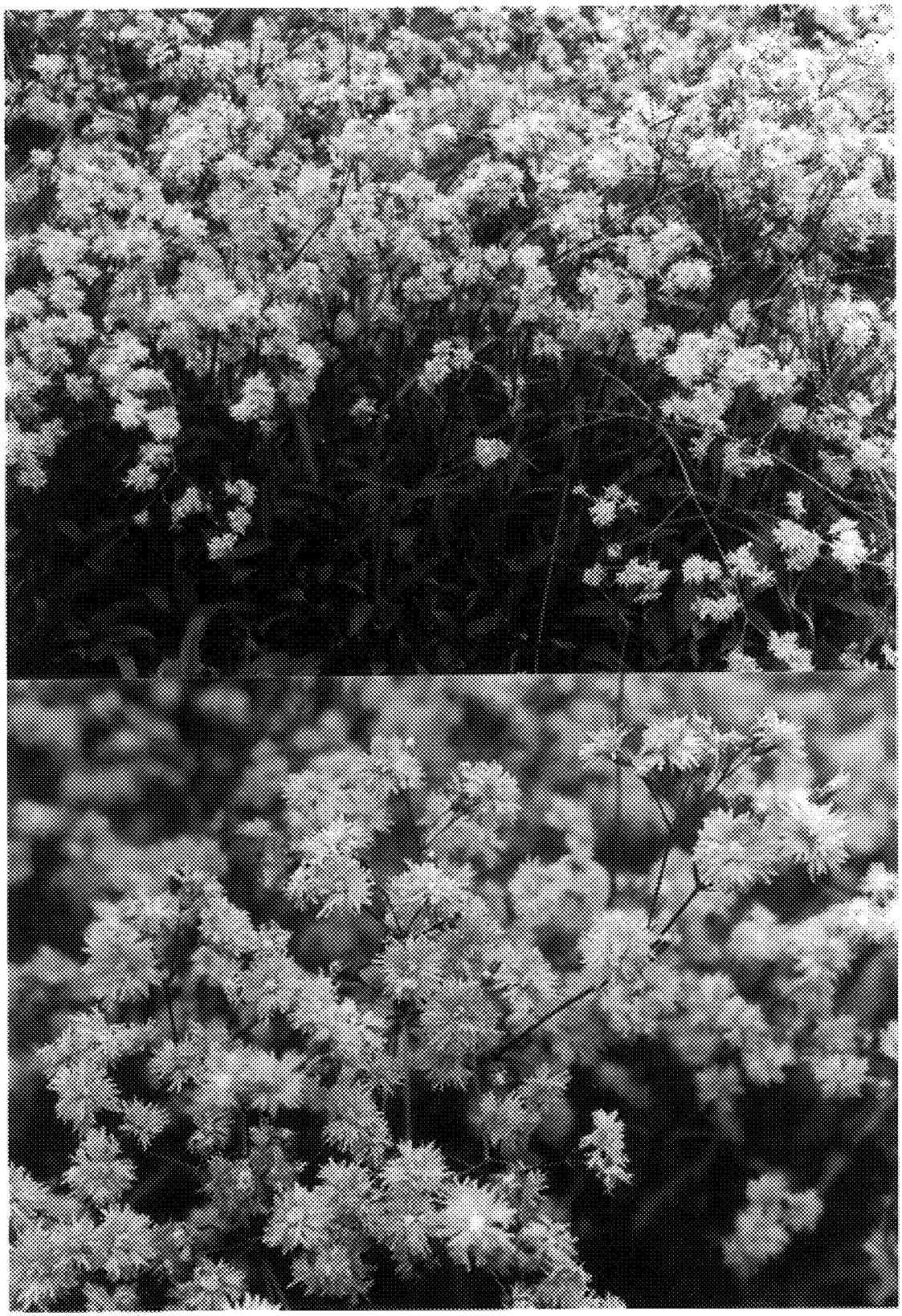

* * * * *